(12) United States Patent
Goldberg

(10) Patent No.: US 7,402,438 B2
(45) Date of Patent: Jul. 22, 2008

(54) AUTOMATED IDENTIFICATION OF CARBOHYDRATES IN MASS SPECTRA

(75) Inventor: David Goldberg, Palo Alto, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 666 days.

(21) Appl. No.: 10/696,814

(22) Filed: Oct. 30, 2003

(65) Prior Publication Data
US 2005/0096851 A1    May 5, 2005

(51) Int. Cl.
*G01N 24/00*  (2006.01)
*G01N 33/00*  (2006.01)
*G05B 21/00*  (2006.01)

(52) U.S. Cl. .................. 436/173; 436/94; 700/273

(58) Field of Classification Search .......... None
See application file for complete search history.

(56) References Cited

U.S. PATENT DOCUMENTS

2002/0102610 A1  8/2002  Townsend et al. ............. 435/7.1
2003/0027216 A1  2/2003  Kiernan et al. ............... 435/7.1

OTHER PUBLICATIONS

Goldberg et al. "Automated annotation of matrix-assisted laser desorption/ionization N-glycan spectra", Proteomics, 2005, v. 5, pp. 855-875.*
Lohmann et al. "Glyco-Fragment: a web tool to support the interpretation of mass spectra of complex carbohydrates", Proteomics, Jul. 2003, v. 3, pp. 2028-2035.*
Yergey et al. "Isotopic distributions in mass spectra of large molecules", Anal. Chem., 1983, v. 55, pp. 353-356.*
Dell et al. "Glycoprotein structure determination by mass spectrometry", Science, 2001, v. 291, pp. 2351-2356.*
Cooper et al. "GlycoSuiteDB: a new curated relational database of glycoprotein glycan structures ad their biological sources", Nucleic Acids Research, 2001, v. 29, No. 1, pp. 332-335.*
Lohmann et al. "GlycoFragment and GlycoSearch MS: web tools to support the interpretations of mass spectra of complex carbohydrates", Nucleic Acids Research, 2004, v. 32, Web Server Issue, W261-W266.*
von der Lieth et al. "Bioinformatics for glycomics: status, methods, requirements and perspectives", Briefings in Bioinformatics, Jun. 2004, v. 5, No. 2, pp. 164-178.*
Fernández-de-Cossilo et al. "Automated interpretation of mass spectra of complex mixtures by matching of isotope peak distribution", Rapid Comm. Mass Spectrometry, 2004, v. 18, pp. 2465-2472.*
Lütteke et al. "GLYCOSCIENCES.de: an internet portal to support glycomics and glycobiology research", Glycobiology Advance Access, 2005, Oct. 2005, pp. 1-14.*
Goldberg et al. "Automatic determination of O-glycan structure from fragmentation spectra", Proteomics, 2006, v. 5, pp. 1429-1434.*
David J. Harvey, "Identification of protein-bound carbohydrates by mass spectrometry", Proteomics 2001, 1, pp. 311-328.

* cited by examiner

*Primary Examiner*—Yelena G Gakh
(74) *Attorney, Agent, or Firm*—Fay Sharpe LLP

(57) ABSTRACT

Disclosed is a computerized method for identifying peaks corresponding to glycans from a mass spectrum. At least one glycan spectrum is received from a mass spectrometer, with each glycan spectrum including peaks having a measured mass. Glycan identifications are automatically assigned to each of the peaks and these assignments are then reported.

22 Claims, 6 Drawing Sheets

AUTOMATED IDENTIFICATION OF CARBOHYDRATES IN MASS SPECTRA

INCORPORATION BY REFERENCE

The following U.S. patent application publications are fully incorporated herein by reference: U.S. Patent Application Publication No. 2002/0102610 ("Automated Identification of Peptides"); and U.S. Patent Application Publication No. 2003/0027216 ("Analysis of Proteins from Biological Fluids Using Mass Spectrometric Immunoassay").

BACKGROUND

This disclosure relates to computer-mediated devices and methods for automated interpretation of data obtained by mass spectrometry in order to identify carbohydrates, particularly carbohydrates covalently bonded with proteins.

Since the genes in an organism encode the list of proteins that the organism manufactures, in principle the complete genome sequence of an organism provides a complete list of proteins in that organism. However, proteins are often modified after they are constructed from the gene (DNA) template, and these modifications have biological significance. Perhaps the most important class of modifications is the addition of small carbohydrates (glycans) to the protein. An example illustrating the importance of these modifications are the human blood groups, which result from the attachment of glycans to molecules on the surface of blood cells. A key problem in proteomics is the identification of these glycans. However, no practical automated method for identifying these glycans is currently available. Such a method would facilitate the labeling of peaks in a spectra and the identification of patterns that may not be readily observed from a non-automated process.

BRIEF SUMMARY

The disclosed embodiments provide examples of improved solutions to the problems noted in the above Background discussion and the art cited therein. There is shown in these examples an improved method and system for identifying peaks corresponding to glycans from a mass spectrum, which may provide some or all of the following features. At least one glycan spectrum is received from a mass spectrometer, with each glycan spectrum including peaks having a measured mass. Glycan identifications are automatically assigned to each of the peaks and these assignments are then reported. In one embodiment, the glycan identifications are in the form of cartoons, that is, a cartoon is associated to peaks of the spectra.

In another embodiment there is disclosed a computerized system for identifying peaks corresponding to glycans from a mass spectrum. The system includes a spectrum receiver for transmitting spectrum files to the system, with each spectrum file including a set of masses (or mass ranges) and the ion frequency for each mass (or mass range). A maketable module constructs a monosaccharide set table, in which each row of the table represents a set of monosaccharides. An identification module develops a listing of mass peaks in the spectrum which match a row from the monosaccharide set table. A summary module structures a glycan report. Memory modules include a monosaccharide set table module, a peak identification file module, a cartoon library, in which reside symbolic representations of specific isomers, and a glycan report file module.

In yet another embodiment, there is disclosed an article of manufacture in the form of a computer usable medium having computer readable program code embodied in the medium. When the computer executes the program code, the computer is caused to perform method steps for identifying peaks corresponding to glycans from a mass spectrum. At least one glycan spectrum is received from a mass spectrometer, with each glycan spectrum including peaks having a measured mass. Glycan identifications are automatically assigned to each of the peaks and these assignments are then reported.

BRIEF DESCRIPTION OF THE DRAWINGS

The foregoing and other features of the embodiments described herein will be apparent and easily understood from a further reading of the specification, claims and by reference to the accompanying drawings in which:

DETAILED DESCRIPTION

Figure 1:
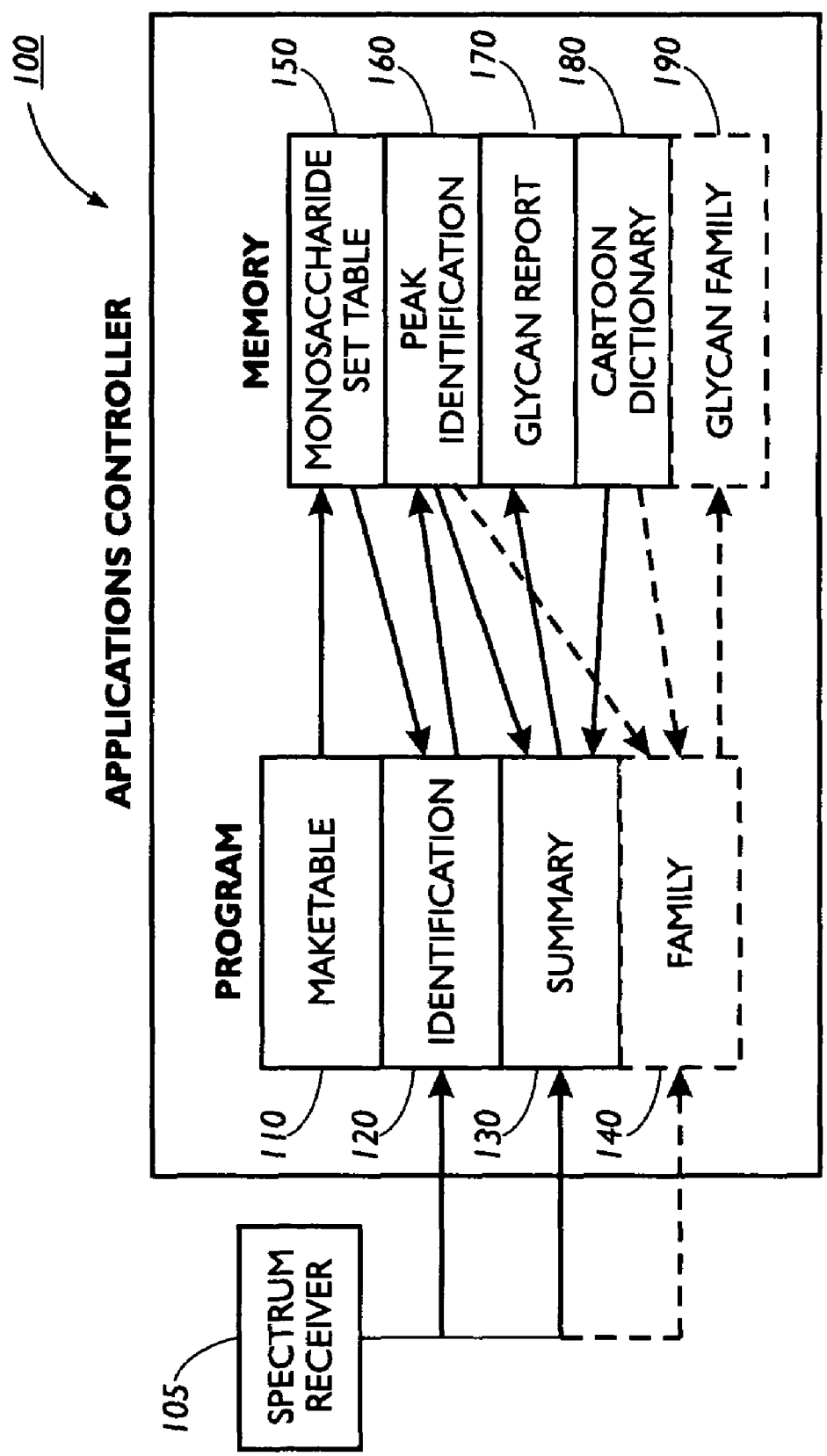
FIG. 1 is a simplified diagram illustrating one embodiment of the glycans identification system disclosed herein.

As used herein, the term "mass spectrometer" refers to a device able to volatilize/ionize analytes to form vapor-phase ions and determine their absolute or relative molecular masses. Suitable forms of volatilization/ionization are laser/light, thermal, electrical, atomized/sprayed and the like or combinations thereof. Suitable forms of mass spectrometry include, but are not limited to, matrix Assisted Laser Desorption/Time of Flight Mass Spectrometry (MALDI-TOF MS), electrospray (or nanospray) ionization (ESI) mass spectrometry, or the like or combinations thereof.

As used herein, a "display" means any device or artefact that presents information in a form intelligible to a human observer and includes, without limitation, a computer terminal, a computer screen, a screen upon which information is projected, and paper or other tangible medium upon which information is temporarily or permanently recorded, whether by printing, writing or any other means.

As used herein, "list" means a computer-readable representation of data. A list may be implemented as any desired data structure, including without limitation a table, stack or array. A list may if desired be stored as a file or as a plurality of files.

As used herein, the term "protein" means any one of a group of large organic molecules containing chiefly carbon, hydrogen, oxygen, nitrogen and sulphur and consisting of unbranched chains constructed from a set of approximately twenty different amino acids, with one or more such polypeptide chains comprising a protein molecule.

As used herein, the term "carbohydrate" means any member of a large class of chemical compounds that includes sugars, starches, cellulose, and related compounds, including monosaccharides, disaccharides, oligosaccharides, and polysaccharides.

As used herein, the term "glycan" means polymers of more than about ten monosaccharide residues linked glycosidically in branched or unbranched chains.

As used herein, the term "isomer" means one of two or more compounds having the same monosaccharide compositions but different structures. A cartoon is a symbolic representation that is used to describe different structures. That is, different isomers are represented by different cartoons.

As used herein, the term "isotope" means one of two or more atoms having the same atomic number but differing in atomic weight and mass number.

This disclosure provides a system and method for automating the identification of glycans from a mass spectrum. In a sample of glycans processed through a mass spectrometer, the program identifies the glycans present in the sample by labeling the peaks in the spectra with cartoons of the glycans they represent. Some important features of the program are (1) it doesn't require the biologist to estimate the accuracy of the spectrum analyzer—this may be determined automatically; (2) glycan assignments may be associated with a confidence score; (3) the set of possible glycans is customizable. This last capability is desirable, since the set of possible glycans is different in different organisms (or even different tissues within a single organism).

Turning now to the drawings, wherein the purpose is for illustrating the embodiments of the system and method, and not for limiting the same, FIG. 1 illustrates a portion of a computing environment for performing glycan identification. It will be appreciated that various computing environments may incorporate glycan identification. The following discussion is intended to provide a brief, general description of suitable computing environments in which the glycan identification method and system may be implemented. Although not required, the method and system will be described in the general context of computer-executable instructions, such as program modules, being executed by a networked computer. Generally, program modules include routines, programs, objects, components, data structures, etc., that perform particular tasks or implement particular abstract data types. Moreover, those skilled in the art will appreciate that the method and system may be practiced with other computer system configurations, including hand-held devices, multiprocessor systems, microprocessor-based or programmable consumer electronics, networked PCs, minicomputers, mainframe computers, embedded processors and the like. The method and system may also be practiced in distributed computing environments where tasks are performed by remote processing devices that are linked through a communications network. In a distributed computing environment, program modules may be located in both local and remote memory storage devices.

It will be recognized that a computing environment may include various modules, such as a processing unit, system memory, a system bus coupling various system components to the processing unit, an input/output system, a hard disk drive, an optical disk drive, program modules, program data, monitor, various interfaces, peripheral output devices, and/or networked remote computers. However, for the purpose of clarity, FIG. 1 illustrates only those modules within the computing environment which interact with the glycan identification program. In particular, the glycan identification program resides within a computing module, which includes a processing unit, operating system, applications module, and memory module. The memory module may be comprised of one or more of disk storage, tape storage, magnetic media, non-volatile memory, EPROM memory, EEPROM memory, FLASH memory, DRAM memory, SRAM memory, ROM, CD memory, computer memory, and/or any like memory system or device. The applications module may perform many possible tasks, one of which is glycan identification. The embodiments of the glycan identification method and system described herein are exemplary only and do not limit the function of the glycan identification method and system to those specific tasks or sequences of task performance.

In FIG. 1, glycan identification system 100 includes both program and memory components. Program component 110, the marketable program, constructs a monosaccharide set table, described in greater detail with reference to FIG. 4, which is saved in memory file 150. This table is customizable, as explained below.

Figure 2:
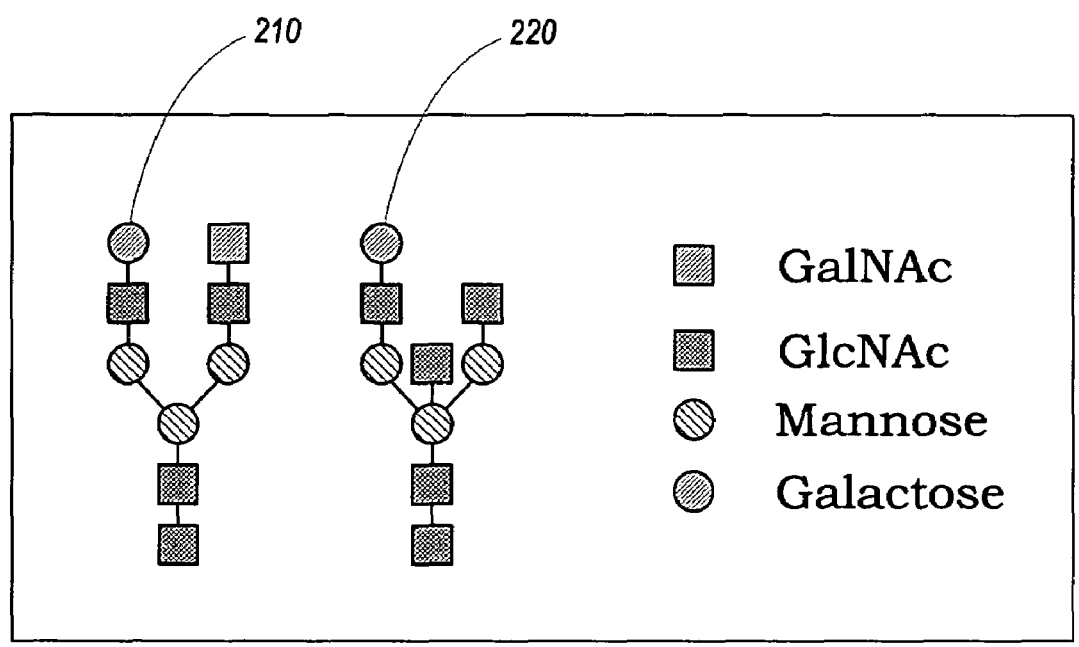
FIG. 2 is a simplified pictorial illustration of example cartoons from a cartoon library.

The monosaccharide set table is composed of potential glycans generated by using all possible sets of monosaccharides within a range set by the experimenter. Each row of the table contains a set of potential glycan isomers, its theoretical mass, and the probability of each isotope. So each row of the monosaccharide table represents a set of glycan isomers, i.e., the different isomers that are comprised of that particular set of monosaccharides. For example, if a row of the table specifies 5 HexNAcs and 4 Hexoses, it would represent all glucans (isomers) with that composition. FIG. 2 illustrates two such isomers. The symbolic representation shown in that figure is called a cartoon. The two cartoons represent two clearly different molecules, even though they have the same monosaccharide composition and correspond to the same row of the monosaccharide table.

The identification component 120 reads monosaccharide set table 150 and a spectrum file from the spectrum receiver 105 and develops a listing of peaks in the spectrum that match a row from the monosaccharide table, and saves it in peak identification file 160.

Typically the spectrum received from the spectrum analyzer is in the form of a digital representation of a histogram. For each mass (or mass range) the digital representation contains a count of the ions or a number proportional to the count, measured in that range. For the purposes of example, following is a sample digital representation for part of an example spectrum:

| Ind | Mass | Lower Bd | Upper | z | Ht | Rel Inten | Area |
|---|---|---|---|---|---|---|---|
| 1 | 497.316927 | 497.27 | 497.42 | 6 | 2065 | 4.80 | 1592.22 |
| 2 | 497.493638 | 497.42 | 497.56 | 6 | 1468 | 3.42 | 762.34 |
| 3 | 497.661885 | 497.56 | 497.71 | 3 | 1480 | 3.44 | 1174.01 |
| 4 | 497.994684 | 497.71 | 498.26 | 3 | 3495 | 8.13 | 21512.71 |
| 5 | 498.314042 | 498.26 | 498.43 | 3 | 1547 | 3.60 | 1846.14 |
| 6 | 498.476933 | 498.43 | 498.52 | 0 | 1264 | 2.94 | 656.06 |
| 7 | 498.600191 | 498.52 | 498.67 | 0 | 1367 | 3.18 | 923.73 |
| 8 | 499.002176 | 498.67 | 499.25 | 3 | 3212 | 7.47 | 18388.34 |
| 9 | 499.349739 | 499.25 | 499.42 | 3 | 1367 | 3.18 | 526.17 |
| 10 | 499.459394 | 499.44 | 499.50 | 1 | 1480 | 3.44 | 482.20 |

Summary component 130 reads peak identification file 160 and utilizes cartoon library 180 to associate a cartoon with corresponding peaks, then summary component 130 creates a glycan report, which may be sent to a print file or saved as glycan report file 170.

The cartoon library 180 is a compiled set of symbolic representations of glycan isomers used to identify peaks on a spectrum. The library includes a cartoon for most rows of the monosaccharide set table. Each cartoon may have associated program code. While some rows in the table will not have a cartoon, others may have more than one, as is illustrated in FIG. 2. In this example the isomer with 5 HexNAcs and 4

Hexoses might have the two cartoons 210 and 220, respectively. The cartoon library is a subset of all possible cartoons, and contains only biosynthetically plausible cartoons.

In developing the cartoon library 180, an initial set of cartoon archetypes are loaded into the library by the user. From these initial cartoon archetypes, the library is expanded using a set of rules. These rules specify the combinations that result in isomers of the same glycan. Therefore, each archetype can generate multiple cartoons for the library. These rules may be structured such that they rarely generate a biosynthetically implausible cartoon. For example, two sample rules are:

"A NeuAc can always be replaced by a NeuGc" and "If there is a single fructose at the reducing end of a glycan, it can always be removed."

The rules may not necessarily directly correspond to a biosynthetic pathway. Instead they may take a set of cartoons and reduce it to a single exemplar and a rule for generating the rest of the set. Note that the rules may need to be applied repeatedly. For example, if a glycan has two sialic acids, then the first rule generates three variants: NeuAc/NeuAc, NeuAc/NeuGc, and NeuGc/NeuGc. The rules may be species or tissue specific. Changing the rules is one way of performing customization of the table.

Returning to FIG. 1, an optional family program component 140 provides functionality that can be used in addition to or instead of summary component 130. Family component 140 utilizes the information from peak identification file 160 and the cartoon library to develop a glycan family file 190 in which each family is represented as labels to a spectrum. Multiple families may be represented as labels on a single spectrum or each on its own spectrum. For the purposes herein, a family is a sequence of spectrum peaks, with the label for each peak containing one more monosaccharide than the label of the preceding peak. This functionality visualizes the steps by which the glycan is synthesized, monosaccharide by monosaccharide. The family report file may then be sent to a print file or saved as glycan family file 190.

Figure 3:
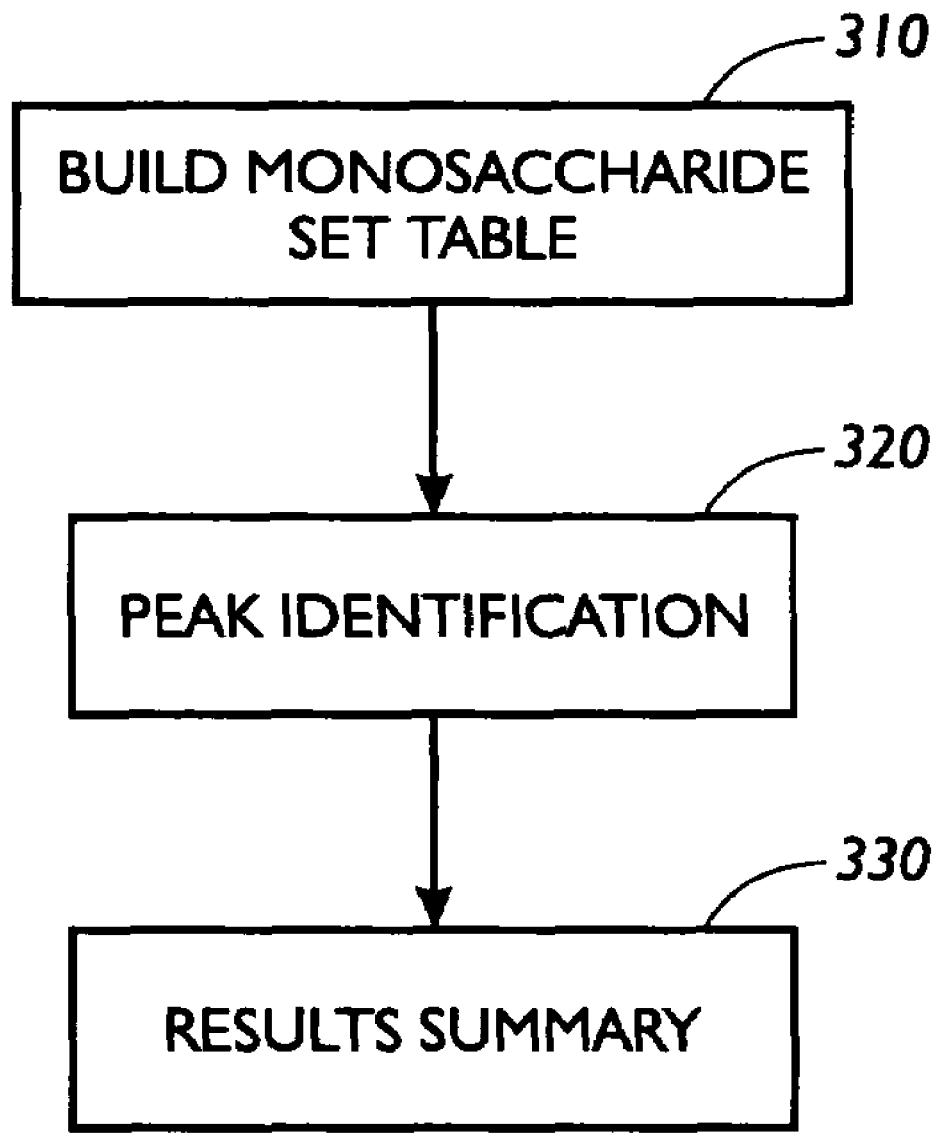
FIG. 3 is a simplified flow diagram of an embodiment of the method for automated identification of glycans.

Turning now to FIG. 3, there is illustrated an example embodiment of the automated method for glycan identification. At 310 a monosaccharide set table, which is discussed in greater detail with reference to FIG. 4 hereinbelow, is constructed through use of a program such as, for example, maketable described hereinabove, to include the sets of monosaccharides and their masses. At 320, peak identification and assignment, described more fully hereinbelow with reference to FIG. 5, is performed. The results from peak assignment 320 are combined with cartoons at results summary 330 to produce a glycan report, which may be saved or sent to a print file. The glycan report may be in the form of a plain-text report and is illustrated graphically. In these graphical reports, assignments may only be reported if they correspond to a glycan that has a corresponding cartoon in the cartoon library.

Figure 4:
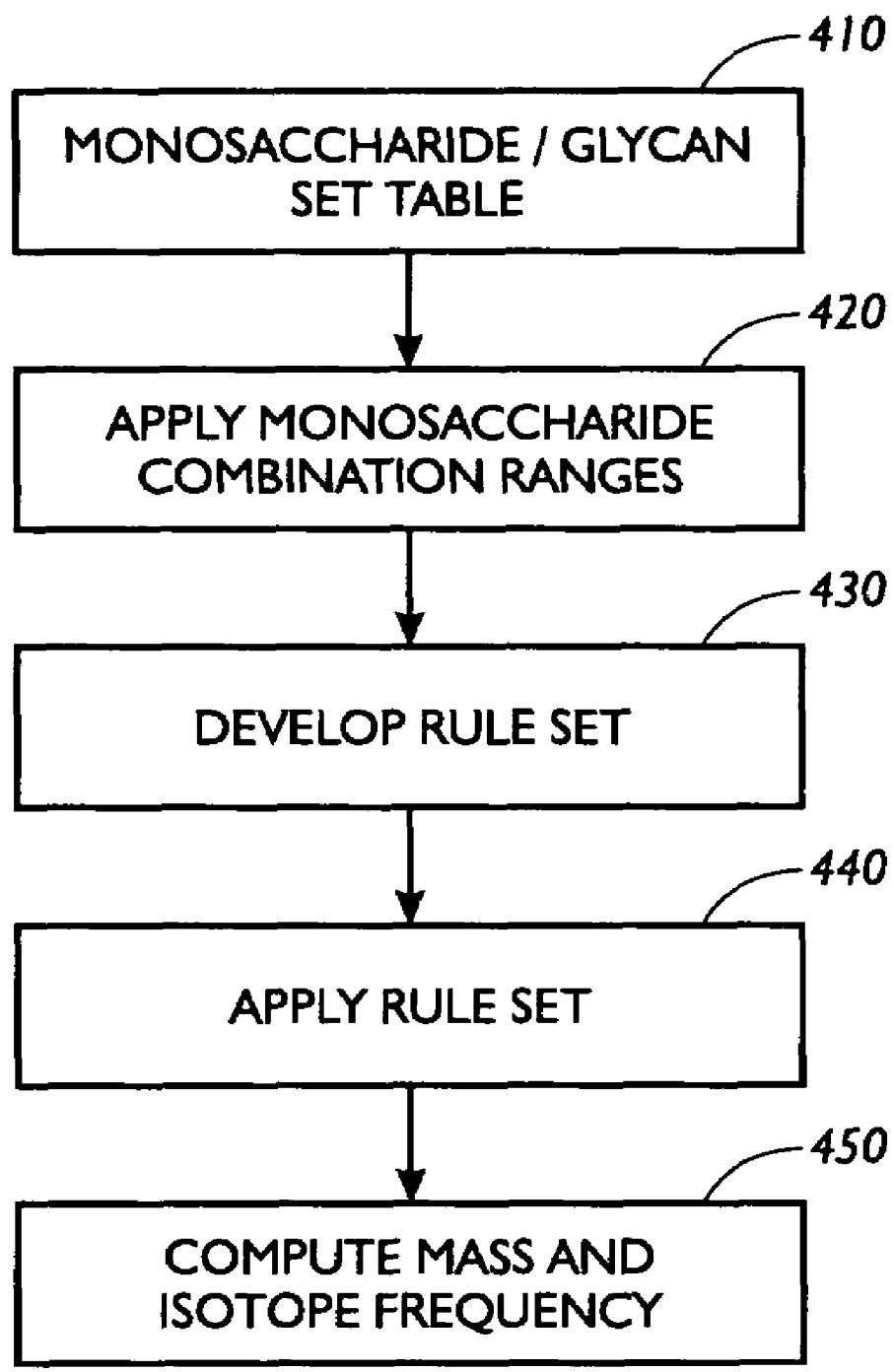
FIG. 4 is a simplified flow diagram of an embodiment of a method for construction of a monosaccharide set table.
Figure 5:
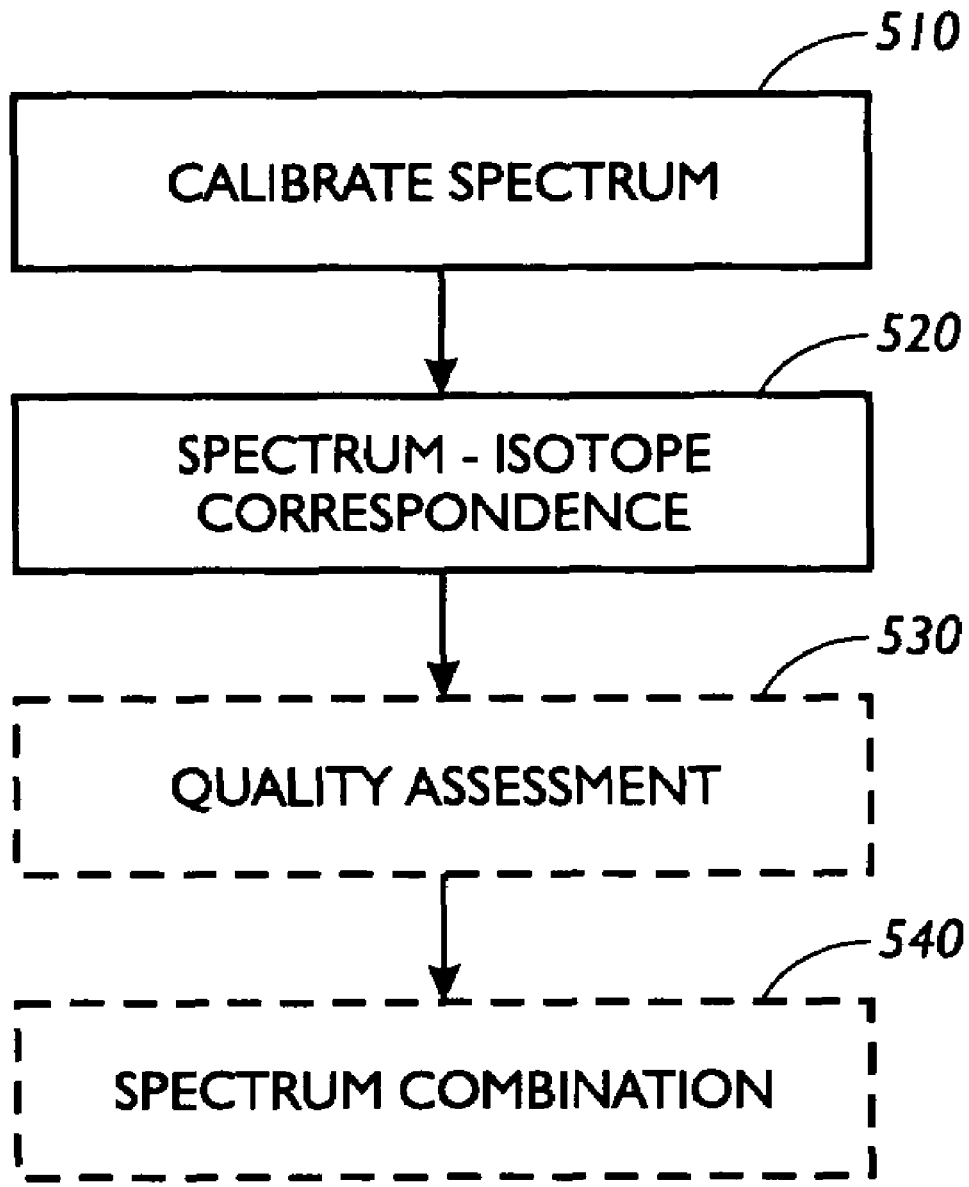
FIG. 5 is a simplified flow diagram of an embodiment of the method for peak identification.

Turning now to FIG. 4, an embodiment for construction of the monosaccharide set table is discussed in more detail. At 410, a table in the following form is structured,

| HexNAc | Hexose | fucose | NeuAc | NeuGc |
|--------|--------|--------|-------|-------|
| 2 | 3 | 0 | 0 | 0 |
| 2 | 3 | 1 | 0 | 0 |
| 2 | 4 | 0 | 0 | 0 |
| 3 | 3 | 0 | 0 | 0 |
| ... | ... | ... | ... | ... | in which each row represents all isomers with the given atomic composition for the glycan. At 420, a row is generated for each possible combination of the monosaccharides using the following ranges:

|  | Min | Max |
|---|---|---|
| HexNAc | 2 | 8 |
| Hexose | 3 | 13 |
| fucose | 0 | 6 |
| NeuAc | 0 | 4 |
| NeuGc | 0 | 4 |

Rows are then evaluated according to a rule set formulated at 430. For example, one such set of possible rules could be:

fucose $\leq$ # Hexose+# HexNAc−4

HexNAc $\leq$ # Hexose+6

NeuAc+# NeuGc $\leq$ 2 min ((# Hexose−3, # HexNAc−2)

Changing these rule sets is one way of performing customization of the tables. The rule set is applied at 440 and rows are eliminated if they don't satisfy all of a set of specified rules. After the rows are generated, the mass of each row is computed, together with the frequency of its isotopes (i.e., its relative abundance), at 450. The isotope frequencies are computed based on the isotopic frequencies for H, C, O and N. So the first few rows of the above example, with their masses, become

| | | | | | | Probability of Each Isotope | | | | |
|---|---|---|---|---|---|---|---|---|---|---|
| HexNAc | Hexose | fucose | NeuAc | NeuGc | Mass | +0 | +1 | +2 | +3 | +4 |
| 2 | 3 | 0 | 0 | 0 | 1171.58 | 0.524 | 0.313 | 0.119 | 0.034 | 0.008 |
| 2 | 3 | 1 | 0 | 0 | 1345.67 | 0.474 | 0.327 | 0.140 | 0.044 | 0.011 |
| 2 | 4 | 0 | 0 | 0 | 1375.68 | 0.467 | 0.328 | 0.143 | 0.046 | 0.012 |
| 3 | 3 | 0 | 0 | 0 | 1416.71 | 0.455 | 0.332 | 0.147 | 0.049 | 0.013 |
| . | . | . | . | . | . | . | . | . | . | . |
| . | . | . | . | . | . | . | . | . | . | . |

Turning now to FIG. 5, one example embodiment of peak identification is illustrated. The method estimates the precision and calibration of a spectrum automatically at 510. Although for the purposes of example, calibration of the spectrum has been performed automatically, the user may set the calibration explicitly. For automatic calibration, some high-confidence peak identifications are made and the relative difference between observed and predicted masses of these identifications is measured. As an example, suppose the measured mass of each of these peaks is between 200 and 300 ppm below the theoretical mass of its assigned glycan. Then when deciding whether to assign a glycan to one of the other peaks there is greater confidence in the assignment if the observed peak is between 200-300 ppm below the predicted mass of the glycan. The match is rejected if it is (for example) 200 ppm above the predicted mass. In other words, the spectrum is calibrated by defining an acceptable tolerance based on the tolerance of the high-confidence assignments.

In more detail, taking high-confidence peak identifications and the measured relative difference between observed and predicted masses of the identifications yields two numbers a and b which can be used to decide if an observed peak should be assigned to a glycan. An assignment is accepted if the observed mass and theoretical mass of the glycan satisfy $$\left| \frac{\text{observed} - \text{theoretical} - a}{\text{theoretical}} \right| < b \quad (1)$$

Currently, high confidence identification of a peak with a glycan means
  The peak is intense—it's one of the 200 highest peaks.
  The mass of the peak is within a tolerance t of a theoretical glycan mass m.
  The isotope envelope closely matches the theoretical one.
  There are no significant peaks near mass m−1.

Another possible criterion would be to require that the theoretical glycan be on an approved list of commonly occurring glycans.

Using the relative difference $\Delta$ between theoretical and observed peaks, $$\Delta = \frac{\text{observed} - \text{theoretical}}{\text{theoretical}}$$

In a perfectly calibrated spectrum, about half the $\Delta$'s would be positive and half the $\Delta$'s would be negative. In fact, spectra are rarely perfectly calibrated, and often all the $\Delta$'s have the same sign.

One example approach to compute the constant a in equation (1) hereinabove:
1. Set the tolerance t to 300 ppm
2. Find all high confidence peaks that are within t of the theoretical glycan mass, that is $$|\Delta| < t$$

3. If there are fewer than 15 such peaks, replace t with 2t and go back to step 2.
4. Compute the relative difference $\Delta$ for each high confidence peak and compute the median $\Delta_{med}$ of all the $\Delta$'s. This is a measure of calibration error and is a first estimate for the constant a.
5. Apply an adjusted formula for $\Delta$ that takes into account the calibration error $$\Delta = \frac{\text{observed} - \text{theoretical} - \Delta_{med}}{\text{theoretical}}$$

Find an improved set of high confidence peaks, namely those with $|\Delta| < t$ using this new definition of $\Delta$.
6. Repeat steps 4 and 5 until they resolve to provide a consistent value of $\Delta_{med}$. Then set $a = \Delta_{med}$.

One possible approach for determining a reasonable value for b is achieved by setting t to 10 ppm and increasing it in increments of 10 ppm, for each t a set $\{\Delta_i\}$ of the relative differences of the peaks within tolerance t is computed. In trying to detect the point at which the $\Delta_i$'s no longer reflect the natural noisiness of the mass spectrometer, a point may be reached at which peaks are included that are incorrect assignments. If this "breakdown" occurs for $t = t_0$, then b is set to $b = t_0$.

This "breakdown" may be detected as follows: For each t, an $\chi^2$ test is performed on the resulting $\Delta_i$ to determine if their distribution is normal. If there is a sudden jump in $\chi^2$ at $t = t_0$, the b is set to $b = t_0$. Otherwise the spread of the $\Delta$'s is determined by computing their standard deviation s. For each t, t/s is computed. If there is a value $t_0$ at which t/s has a pronounced maximum, then b is set as $b = t_0$. Otherwise b is selected to be the point at which the standard deviations s seem to reach a plateau. After the spectrum is calibrated, peak assignments are made at 520. Working from the table of isotopes, each entry in the monosaccharide set table is examined, to find a match in the spectrum. This is accomplished by selecting the isotope of each isomer with the highest expected frequency, and then searching the spectrum for a peak within an acceptable tolerance of that isotope. If several possible peaks match within an acceptable tolerance, the peak that gives the best isotope envelope (more precisely, the one with the lowest S score) is selected. This generates a list of assignment of peaks in glycans.

A sample output of peak identification may appear as follows:

| predict m | observ m | off | rank | Diff | #dif | ad | nac | hex | fuc | neuac | neugc | S | nubra | gnbrs |
|---|---|---|---|---|---|---|---|---|---|---|---|---|---|---|
| 2563.29 | 2563.74 | 1 | 2 | −0.45 | −0.00018 | 1.0 | 4 | 4 | 4 | 0 | 0 | 0.01 | 5 | 5 |
| 2565.27 | 2565.75 | 1 | 8 | −0.48 | −0.00019 | 1.2 | 3 | 6 | 1 | 1 | 0 | 0.28 | 7 | 1* |
| 2565.27 | 2565.75 | 1 | 8 | −0.48 | −0.00019 | 1.2 | 3 | 5 | 2 | 0 | 1 | 0.28 | 8 | 1* |
| 3042.52 | 3042.83 | 1 | 12 | −0.31 | −0.00010 | 0.6 | 5 | 6 | 3 | 0 | 0 | 0.01 | 8 | 6 |
| 2389.20 | 2389.73 | 1 | 13 | −0.53 | −0.00022 | 2.0 | 4 | 4 | 3 | 0 | 0 | 0.02 | 8 | 3 |
| 2838.42 | 2838.79 | 1 | 16 | −0.37 | −0.00013 | 0.0 | 5 | 5 | 3 | 0 | 0 | 0.01 | 8 | 5 |
| 2593.30 | 2593.78 | 1 | 32 | −0.48 | −0.00018 | 1.2 | 4 | 5 | 3 | 0 | 0 | 0.01 | 8 | 6 |
| 3044.50 | 3044.83 | 1 | 37 | −0.33 | −0.00011 | 0.5 | 4 | 7 | 1 | 0 | 1 | 0.37 | 9 | 0* |
| 3044.50 | 3044.83 | 1 | 37 | −0.33 | −0.00011 | 0.5 | 4 | 8 | 0 | 1 | 0 | 0.37 | 8 | 1* |

-continued

| predict m | observ m | off | rank | Diff | #dif | ad | nac | hex | fuc | neuac | neuge | S | nubra | gnbrs | |
|---|---|---|---|---|---|---|---|---|---|---|---|---|---|---|---|
| 2391.18 | 2391.70 | 1 | 49 | −0.52 | −0.00022 | 1.8 | 3 | 5 | 1 | 0 | 1 | 0.57 | 8 | 0* | s |
| 2391.18 | 2391.70 | 1 | 49 | −0.52 | −0.00022 | 1.8 | 3 | 6 | 0 | 1 | 0 | 0.57 | 7 | 0* | s |
| 3012.51 | 3012.80 | 1 | 54 | −0.29 | −0.00009 | 0.7 | 5 | 5 | 4 | 0 | 0 | 0.05 | 8 | 7 | |
| 3014.49 | 3014.80 | 1 | 58 | −0.31 | −0.00010 | 0.5 | 4 | 7 | 1 | 1 | 0 | 0.16 | 9 | 2* | |
| 3014.49 | 3014.80 | 1 | 58 | −0.31 | −0.00010 | 0.5 | 4 | 6 | 2 | 0 | 1 | 0.16 | 9 | 3* | |

Peak identification may optionally include quality assessment, as shown at 530. If this option is selected, each assignment is rated based on a quality score measurement, which determines the likelihood that the assignment is correct. This is based on several factors:

1. Proximity of the measured mass of the peak to the theoretical mass of the glycan. This may be measured by $$\left| \frac{\text{observed} - \text{theoretical} - a}{\text{theoretical}} \right|$$

where $\alpha = \Delta_{med}$

2. Computation of the isotope envelops. Theoretical frequencies $f_i$ were computed when the monosaccharide set table was constructed. For each peak of mass m, the peak heights at m, m+1, ... m+5 are checked and converted to frequencies $f'_i$. The observed and theoretical frequencies are compared using $$S = \Sigma (f_i - f'_i)^2.$$

Smaller values correspond to higher-quality matches.

3. Examination of m−1 peak. If a peak occurs at m−1, the height of this peak is checked. A smaller peak height is an indication of confidence in the assignment.

Although these factors may be combined into a quality number, they may also be utilized in a binary form to indicate a suspect peak. A peak is suspect if either $$\left| \frac{\text{observed} - \text{theoretical} - a}{\text{theoretical}} \right| > 3s,$$

in which s is the standard deviation of the theoretical high confidence assignments), or if the isotope sum S>0:30, or if the height of the peak at m−1 is greater than one-half the height of the highest theoretical isotope peak of the glycan.

In the case in which the spectrum contains peaks for two glycans of nearby mass, the isotope rule may be modified to distinguish nearby glycans.

Another possible option within peak identification is spectrum combination at 540. In a case in which multiple spectra are available, it is possible to combine the information in them to learn more than could be gained from a single spectrum. Although several analyses are available for this case, two examples are described for the purposes of illustration.

1. Are there peaks common to many spectra that don't match any glycan? If so, can they be identified, for example, as a contaminant?
2. Are there glycan isomers that don't have an obvious cartoon (i.e., are biosynthetically implausible), but still appear frequently?

Figure 6:
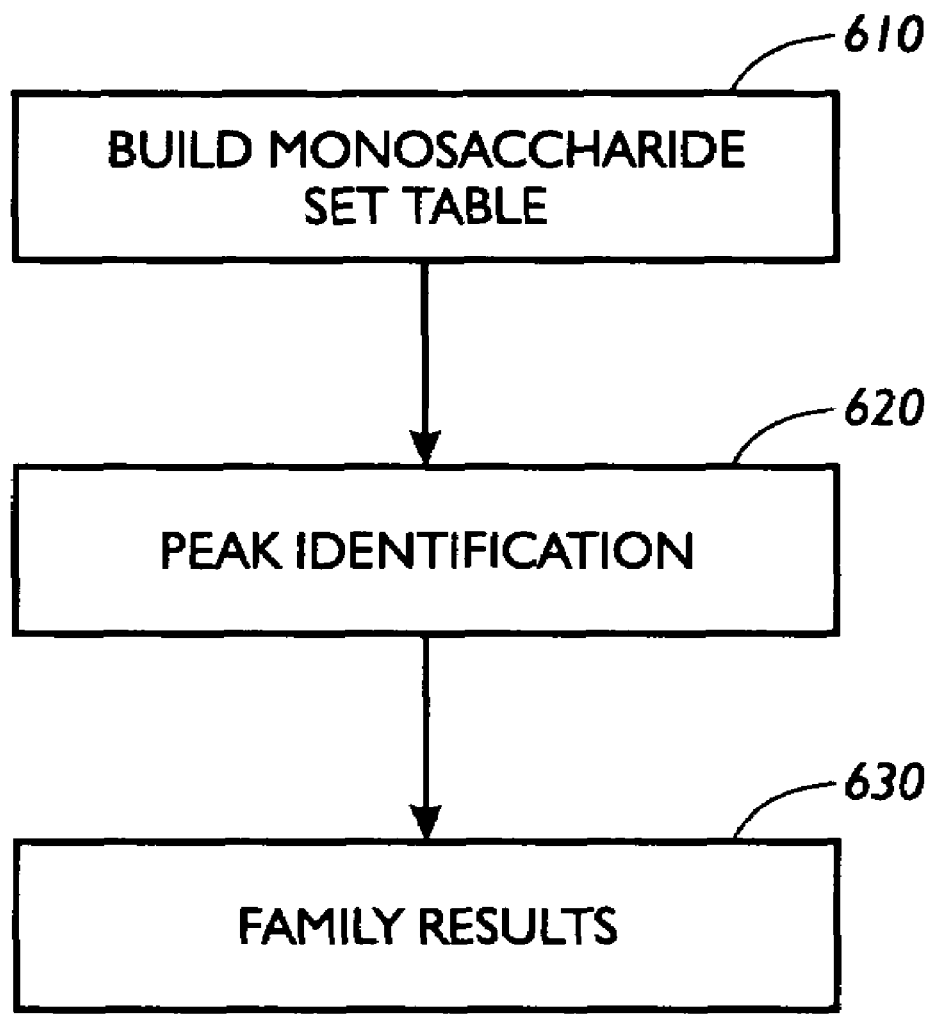
FIG. 6 is a simplified flow diagram of an alternate embodiment of the method for automated identification of glycans.

Turning now to FIG. 6, there is illustrated another example embodiment of the method for automated identification of glycans. At 610 a monosaccharide set table, which is discussed in greater detail with reference to FIG. 4, is constructed through use of a program such as, for example, maketable described hereinabove, to include the isomers and their masses. At 620, peak identification and assignment, described more fully hereinabove with reference to FIG. 5, is performed. The results from peak assignment 620 are combined with cartoons at family results 630 to produce a family report, which may be saved or sent to a print file. The family report may be in the form of a plain-text report in which each family of glycans is reported separately. In those cases in which the report is illustrated graphically, assignments may only be reported if they correspond to a glycan that has a corresponding cartoon in the cartoon library. For the purposes herein, a family is a sequence of spectrum peaks, with the label for each peak containing one more monosaccharide than the label of the preceding peak. This functionality visualizes the steps by which the glycan is synthesized, monosaccharide by monosaccharide.

While the present discussion has been illustrated and described with reference to specific embodiments, further modification and improvements will occur to those skilled in the art. Additionally, "code" as used herein, or "program" as used herein, is any plurality of binary values or any executable, interpreted or compiled code which can be used by a computer or execution device to perform a task. This code or program can be written in any one of several known computer languages. A "computer", as used herein, can mean any device which stores, processes, routes, manipulates, or performs like operation on data. It is to be understood, therefore, that this disclosure is not limited to the particular forms illustrated and that it is intended in the appended claims to embrace all alternatives, modifications, and variations which do not depart from the spirit and scope of the embodiments described herein. The claims, as originally presented and as they may be amended, encompass variations, alternatives, modifications, improvements, equivalents, and substantial equivalents of the embodiments and teachings disclosed herein, including those that are presently unforeseen or unappreciated, and that, for example, may arise from applicants/patentees and others.

What is claimed is:

1. A computerized method for assigning glycans to mass peaks in mass spectra of said glycans, comprising:
    receiving at least one mass spectrum of at least one glycan, wherein at least one of said peaks in said at least one mass spectrum corresponds to a measured mass of said at least one glycan;
    constructing a monosaccharide set table for possible glycans, wherein at least one row represents the monosaccharide composition of at least one possible glycan;
    applying a set of rules generated for the at least one glycan based on experimental and/or biosynthetic conditions, which limit the number of the potential glycans;

eliminating rows from the monosaccharide set table which do not satisfy said set of rules;
calculating at least one theoretical mass for at least one remaining glycan in the monosaccharide set table; and,
assigning at least one glycan to the at least one peak by comparing said measured mass to said theoretical mass.

2. The method according to claim 1, wherein assigning at least one glycan to the at least one peak further comprises annotating said at least one peak with cartoon symbols representing isomeric structures for said at least one glycan, with the cartoons generated from cartoon archetypes.

3. The method according to claim 2, further comprising an automatic computerized estimation of accuracy of glycan assignments by
assigning a confidence score relating to the accuracy of the glycan assignment;
creating a glycan report consisting of the cartoon representation of each corresponding peak with the assigned confidence score; and
reporting to a user the combined peak assignments and cartoons in the form of a glycan report.

4. The method according to claim 3, wherein said set of possible glycans is adjusted depending on the identity of the sample.

5. The method of claim 4, wherein the relative "Δ" difference between a theoretical and observed peak is:

$$\Delta = \left| \frac{\text{observed} - \text{theoretical} - a}{\text{theoretical}} \right|.$$

6. The method according to claim 3, wherein said spectrum is automatically calibrated by measuring the relative difference between the observed and predicted masses of at least one high confidence peak identification.

7. The method according to claim 6, wherein said spectrum is automatically calibrated by defining an acceptable tolerance based on the tolerance of the high-confidence peak assignments.

8. The method according to claim 6, wherein said at least one high confidence peak comprises:
at least one of the 200 highest peaks;
a mass (m) within a set tolerance of a theoretical glycan mass (m), in which no significant peaks are positioned near m−1; and
an isotope envelope closely matching the theoretical one.

9. The method of claim 3, wherein the assignments are accepted if the observed mass and theoretical mass of the glycan satisfy $$\left| \frac{\text{observed} - \text{theoretical} - a}{\text{theoretical}} \right| < b$$

where a and b are obtained by taking a high-confidence peak identifications and the measured relative difference between observed and predicted masses.

10. The method for identifying peaks corresponding to glycans according to claim 3, wherein constructing said monosaccharide set table comprises:
constructing a glycan/monosaccharide set chart, wherein each row represents a set of monosaccharides, further representing a set of possible glycan isomers;
applying combination ranges for a mass of said monosaccharides;
developing said rule set from an initial set of archetypes entered into an associated directory of the cartoons, wherein said rules specify monosaccharide combination limitations;
eliminating each of said monosaccharide rows not satisfying said rule set; and computing glycan isotope frequency based on isotope frequencies for H, C, O, and N and glycan isomer frequency.

11. The method according to claim 1, wherein the step of applying the set of rules comprises:
customizing the set of rules,
wherein said set of rules specify monosaccharide combination limitations.

12. The method according to claim 1, wherein assigning glycan identifications comprises:
defining matches between theoretical masses and spectrum peaks which have a high confidence;
obtaining a tolerance interval for matching from the defined matches,
calibrating spectra using said tolerance interval.

13. The method according to claim 12, wherein the method comprises a step of a preliminary calibration of raw spectra by a user.

14. The method according to claim 12, wherein constructing the monosaccharide set table for potential glycans comprises calculating an isotope envelope for each potential glycan; and wherein defining matches between theoretical masses and spectrum peaks comprises
selecting the isotope with the highest expected frequency from each of said isotope envelopes for each said potential glycan;
searching said spectrum for a peak within an acceptable tolerance of said isotope; and
selecting said peak having the best isotope envelope.

15. The method according to claim 12, further comprising a step of performing a quality assessment to determine the likelihood that said matching of said peaks is correct, wherein said quality assessment is based on factors including proximity of the measured mass to theoretical mass, computation of isotope envelopes, and examination of m−1 peak, wherein when the peak occurs at m−1, the height of the peak is checked and peak height is an indication of confidence in the assignment.

16. The method according to claim 15, wherein computation of isotope envelopes occurs for isotopically labeled or nonlabeled glycans.

17. The method according to claim 1, wherein the step of receiving at least one mass spectrum of at least one glycan comprises receiving a plurality of mass spectra for said glycan, and wherein additional information is obtained from said plurality of spectra from their comparison.

18. The method according to claim 1, further comprising the step of reporting obtained peak assignments, wherein said peak assignments comprises at least one family report, wherein the family comprises a sequence of spectrum peaks, wherein the label for each succeeding peak contains at least one more monosaccharide than the label of the preceding peak.

19. The method according to claim 1, further comprising creating a library of cartoons for the potential glycans generated from archetype cartoons using the set of rules, the library of cartoons containing cartoons representing structural isomers for each potential glycan.

20. The method according to claim 1, wherein constructing the monosaccharide set table for potential glycans comprises calculating isotope abundance for atoms H, C, O, and N, and wherein the step of comparing the measured and theoretical masses takes into account the calculated isotope abundance.

21. The method according to claim 1, wherein constructing the monosaccharide set table for each potential glycan comprises generating all possible combinations of the monosaccharides using predefined ranges for minimum and maximum number of specific monosaccharides for the potential glycan.

22. The method according to claim 1, wherein the step of assigning at least one glycan to the at least one peak further comprises determining the confidence of the peak assignment by selecting the highest peak with an isotope envelope that closely matches its theoretical value.

* * * * *